United States Patent [19]

Wells

[11] 3,967,377
[45] July 6, 1976

[54] PRECISION POSITIONING DEVICE FOR TOOL BLADES AND THE LIKE

[76] Inventor: Royzell F. Wells, 6936 S. Sycamore St., Littleton, Colo. 80120

[22] Filed: Mar. 17, 1975

[21] Appl. No.: 558,709

[52] U.S. Cl. .................................. 30/320; 30/338; 128/305; 33/164 B
[51] Int. Cl.² .......................... B26B 1/08; B26B 5/00
[58] Field of Search .............. 33/170, 154 F, 185 R, 33/164 B; 30/320, 321, 162, 338, 164.9, 293; 279/41, 46, 50, 84; 128/305, 305.1

[56] References Cited
UNITED STATES PATENTS

| 272,944 | 2/1883 | Case | 30/320 X |
|---|---|---|---|
| 2,125,005 | 7/1938 | Jearum | 33/164 B |
| 2,968,489 | 1/1961 | Doniger | 30/162 X |
| 3,247,592 | 4/1966 | Arden | 30/338 |

Primary Examiner—Al Lawrence Smith
Assistant Examiner—J. C. Peters
Attorney, Agent, or Firm—Reilly and Hancock

[57] ABSTRACT

Rotary motion is converted to linear motion by multiple thread sets which cooperate to provide precise control of the amount of rotary motion thus converted. As applied to a precision positioning device for a tool, blade or other object, the thread sets are preferably arranged in a serial and/or telescoped configuration. A relatively simple precision hand tool positioning device is realized by having one thread set arranged in a common direction but reduced pitch relative to the other set. The finiteness of the object positioning is further enhanced by moving it with respect to an inclined plane. A retaining device for gripping the element to be moved is directly associated with a shank having the smaller pitched thread set thereon. The shank is prevented from rotating but allowed to move linearly relative to a housing and the threads thereof engage a spindle which has another set of threads for engaging the housing. A calibrated indicator of the shank position in easily readable format is provided. A split collet for the shank with a spring biased collet clamp and actuator is particularly well-suited for use as a tool chuck especially useful for calibrated craftsman knives. A detent arrangement can be included with the housing.

9 Claims, 8 Drawing Figures

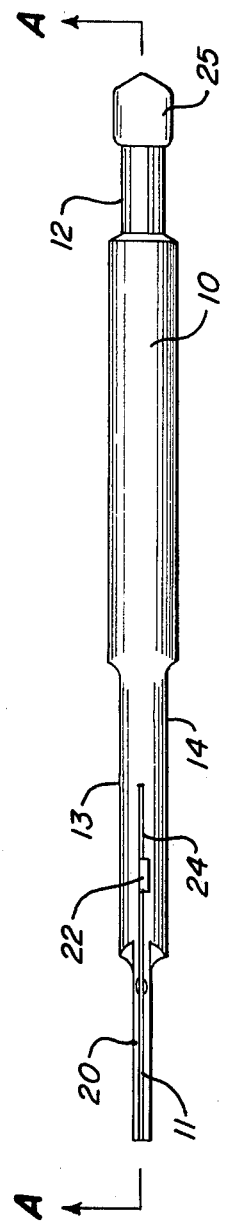
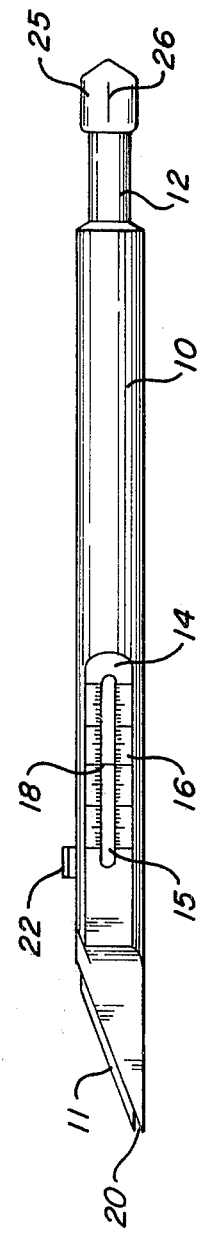

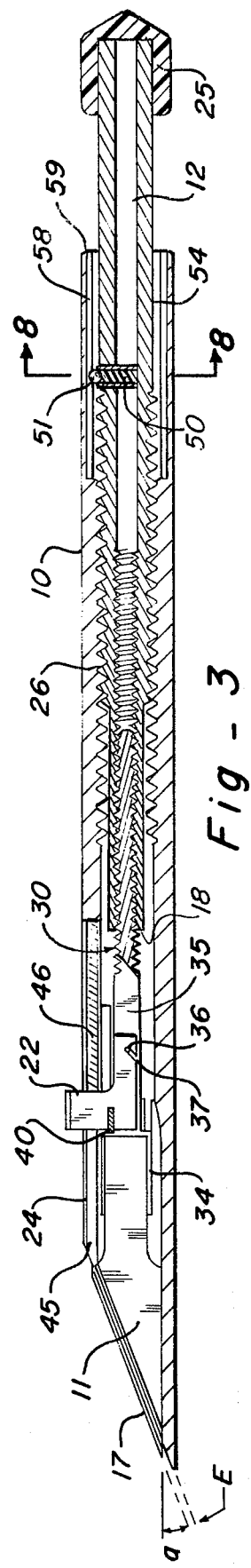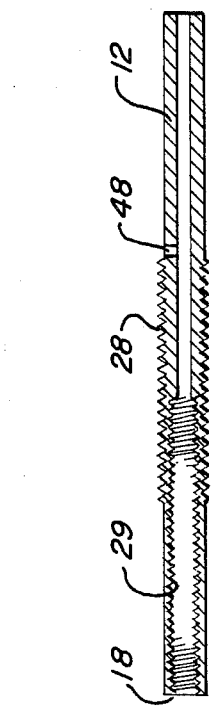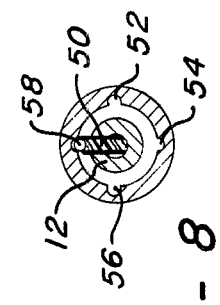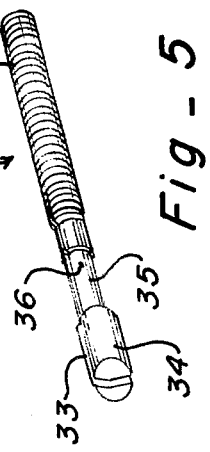

PRECISION POSITIONING DEVICE FOR TOOL BLADES AND THE LIKE

BACKGROUND OF THE INVENTION

This invention relates to devices for precisely positioning an object such as a knife blade, tool, or the like. More particularly, the present invention relates to apparatus for converting rotary motion to linear motion with a precise control of the amount of such conversion. The present invention is particularly useful for exact positioning of a tool element such as a knife blade relative to a housing for that blade.

Various prior art devices have been developed for the purpose of accurately positioning a movable object. One technique for producing this result is obtained by employing a relatively large number of cylindrical threads for a small amount of linear travel. One example is the micrometers which typically employ a very fine thread (forty threads per inch generally) between the spindle and sleeve. One complete revolution of the spindle thus advances or retracts the spindle in the sleeve one-fourtieth or 0.025 inches. Since greater numbers of threads per inch becomes impractical, measurements of linear increments less than 0.025 inches can only be obtained by counting calibration marks around the circumference of the thimble which is attached to the spindle and also surrounds the sleeve.

Further, a variety of devices have been developed for permitting selectable extension of tool elements such as knife blades relative to an enclosing frame. For instance, U.S. Pat. Nos. 1,406,156 by Cotter et al., 1,755,535 by Bratrud, U.S. Pat. No. 1,833,406 by Bratrud and U.S. Pat. No. 3,041,724 by Bobkowski all show various arrangements of internal threading configurations for permitting the extension or withdrawal of knife blades from a housing. Various devices have also been suggested for clamping a tool member relative to a retaining housing. One example of such a device using a threaded shaft mounted coaxially in a housing is shown in U.S. Pat. NO. 3,486,229 by Fischl. Still further, differential threaded arrangements for accurate linear control of rotary to linear motion conversion have been known. For instance, U.S. Pat. Nos. 2,966,170 by Rawlins and 3,409,271 by Kallenbach show such apparatus for valve stem control.

However, none of these devices provide apparatus for easily and reliably positioning a tool element in a precise location short of utilizing a relatively large number of fine cylindrical threads which become impractical for applications requiring movement of thousandths of an inch. Further, there has been a continuing need for a holding device which is adaptable for retaining any of a variety of tools and extending the position of those tools from a retaining frame in a precise manner and with an easily read calibrated indication of the position.

SUMMARY OF THE INVENTION

The present invention employs apparatus including a plurality of sets of cooperating threads which permits precise positioning of an object via rotary to linear motion conversion. As will be described in greater detail below relative to a knife blade extending tool for the preferred embodiment, the device incorporates a rotatable spindle which is threaded into a frame housing and which likewise is threaded onto a chuck or the like. The chuck is retained against rotary motion relative to the housing but is permitted to move coaxially within that housing. By selecting the threads between the chuck and the spindle with a smaller pitch than the threads between the spindle and the frame, a precise amount of movement can be obtained. The interaction between these threads effects a conversion of a rotary motion to relatively small linear motion in a precise manner. A calibrated indication of chuck positioning is provided by including graduated marks along a slot in the housing which cooperates with an edge on the spindle for providing an easily readable scale.

An additional unique feature of the present invention particularly useful as applied for a knife blade extension apparatus is concerned with the clamping chuck arrangement. The clamp chuck actuator prevents rotary motion of the chuck while permitting coaxial linear motion thereof relative to the housing and additionally moves the clamp onto or off of the chuck causing the chuck to grip any object placed between its jaws. Thus the chuck is particularly well suited for gripping any substantially flat or planar object regardless of configuration as long as it fits within the gripping range of the chuck and clamp.

An object of this invention is to provide apparatus for precisely positioning an object to be moved.

Another object of this invention is to provide an arrangement wherein a rotary motion is converted to a precision linear positioning motion.

Still another object of this invention is to provide a planar tool element gripping apparatus which is manually releasable.

A further object of this invention is to provide apparatus for precisely moving a tool element with accurate calibrations of the actual tool movement.

A still further object of this invention is to provide an arrangement for releasably retaining a tool member such as a knife blade or the like while permitting accurate positioning of that tool element by a simple rotary motion.

Yet another object of this invention is to provide a knife blade retaining apparatus which permits withdrawal of the blade edge within a housing frame or extension of that blade edge in a precision position.

The foregoing and other objects, features and advantages of this invention will be more apparent in view of the following description of a preferred embodiment.

BRIEF DESCRIPTION OF THE DRAWINGS

FIG. 1 is a side view of a calibrated knife blade holding apparatus incorporating the structure of the present invention.

FIG. 2 is a top view of the preferred embodiment of FIG. 1.

FIG. 3 is another side view of the preferred embodiment taken along line A—A of FIG. 2 with some elements shown in section.

FIG. 4 is a sectioned view of the spindle for the embodiment.

FIG. 5 is a perspective view of the chuck.

FIG. 6 illustrates the chuck clamp actuator.

FIG. 7 is the chuck clamp; and

FIG. 8 is a section view taken along lines 8—8 of FIG. 3.

DETAILED DESCRIPTION OF THE PREFERRED EMBODIMENT

Although shown and described in terms of a knife blade holding and positioning apparatus in the preferred embodiment, it will be understood that this specific application is illustrated for exemplary purposes only and the invention is not limited to the specific structure shown nor the particular application described. The specific apparatus illustrated comprises a generally cylindrical main frame or body 10 which retains a knife blade 11 and includes a spindle 12 which is used for extension or withdrawal of blade 11 relative to body 10. The main frame or body 10 has two forward flat surfaces 13 and 14 which are substantially parallel. In one flat surface or shoulder portion 14, a slot 15 is included which has a series of calibration marks 16 along each side thereof so that the forward end 18 of spindle 12 can be used to indicate the amount of extension of blade 11 beyond the sloped forward face 20 of main body 10.

As will be described in greater detail later, a chuck clamp actuator 22 extends upwardly from the body 10 and is arranged to move axially within slot 24. Pivotal movement of actuator 22 upwardly results in release of the blade 11 by the chuck so that the blade can be removed and/or positioned as desired. End cap 25 on spindle 12 facilitates the rotation of spindle 12 manually and can also include a guide line 26 for a relatively coarse indication of rotary movement.

The operating interrelationship of the elements of the preferred embodiment can best be seen from the FIG. 3 side view wherein some of these elements are in section or partially sectioned view. The generally tubular main body 10 has a cylindrical threaded portion 26 therewithin which cooperatively engages the external cylindrically threaded sector 28 of spindle 12 as can be seen in the sectioned view of spindle 12 in FIG. 4. As can also be seen in FIG. 4, spindle 12 has an internal sector of internal threads 29 at the forward end 18 thereof.

The chuck 30 as shown in FIGS. 3 and 5 has an external thread segment 31 arranged to cooperatively engage internal threads 29 of spindle 12. The spindle to body threads 26 and 28 are designated as threads T1, with a thread of pitch P1; and, the spindle to chuck threads 29 and 31 are designated as threads T2, with a thread pitch of P2. Both threads are preferably right hand threads. It will be recognized that one of threads 26 and 28 or 29 and 31 can be thread segments rather than complete cylindrical threads if desired.

The spindle to body threads T1 have a larger pitch (coarser threads) than the spindle to chuck threads T2. As the spindle is threaded into the body, the spindle advances one P1 pitch for each complete rotation. Also, for each complete rotation of the spindle, the chuck is retracted into the spindle one P2 pitch. The net result is for each rotation of the spindle the chuck and therefore blade 11 advances one P1 pitch minus one P2 pitch; or advancement = P1−P2, and total advancement = (P1−P2) x number of rotations. However, the cutting edge 17 of the blade 11 and the sloped face 20 of the body 10 are both set at an angle a with respect to the center line of the body and the bottom of slot 24. This angle causes the blade exposure "E", to increase only proportionally to the advancement of the blade. This proportion is equal to the sine trigonometrical function of angle a. Therefore, the blade exposure "E" is equal to the blade advancement times the sine of the angle a, or $E = $ sine a x (P1−P2) x (number of rotations).

As shown in FIG. 5, chuck 30 has a slot 33 which runs through the initial clamping section or jaws 34 and reduced diameter section 35. A hinge pin 36 passes completely through the necked down clamping chuck 31 and is arranged to receive the chuck clamp actuator 22 via slot 37 in actuator 22 as shown in in FIGS. 3 and 6. Actuator 22 has an additional slot 38 on the forward edge thereof. As can be seen in FIGS. 3 and 7, the chuck clamp 40 is a collar having an internally wedge-shaped portion 41 which fits over the reduced section 35 of chuck 30.

Main body 10 has a small bore 45 in the top front end extending through the slot 24 in the body and parallel to the center line of the body. This bore is the recess for actuator spring 46.

When the device is fully assembled, the chuck clamp actuator 22 is retained in the assembly and specifically within the slot 33 of the chuck 30 by the hinge pin 36 of the chuck being engaged in the slot 37 of the actuator 22 and this engagement being maintained by the spring 46. The actuator 22 also engages the chuck clamp 40 via the slot 38 of the actuator and slot 42 of the clamp. The sides of the slot 38 in the actuator serves to raise or lower the clamp 40 onto the chuck 30; and, the slot 42 in the clamp acts against the sides of the actuator to prevent the clamp from rotating around the chuck. The spring 46 also biases the actuator 22 to maintain the clamp 40 in the clamped positions; and, to remove any backlash in the threads T1 and T2.

Before installing a blade 11 in the device, the spindle 12 is preferably turned to the zero position at the calibration marks 16 on the body 10 (FIG. 1). To insert a blade 11 into the device, the actuator 22 is pivoted upwardly and rearwardly to release the wedging force of the clamp 40 from the chuck 30. The blade is inserted through the slot 24 of the body 10 (FIG. 1) and into the jaws 34 of the chuck 30. The back of the blade is bottomed in the slot 24 of the body 10 and the cutting edge 17 of the blade is positioned flush or even with the sloped face 20 of the body. The actuator 22 is then pushed downward causing the clamp 40 to close the chuck jaws 34 onto the blade 11.

A spindle detent arrangement can be included and this is generally illustrated in FIGS. 3, 4 and 8. More particularly, transverse hole 48 extends into spindle 12 and retains the spring loaded ball arrangement 50 therein. The rear bore of the main body 10 includes a series of axially oriented slots or grooves 52, 54, 56 and 58 extending thereinto from the rear end 59. Typically, the detent mechanism 50 consists of a tube containing a ball, a spring and a plunger (not shown). The ball and plunger are retained in the ends of the tube by swagging the ends of the tube. By the arrangement shown, ball 51 will rotate with spindle 12 and provide both a positive feel of each 90° of rotation and a slight retention of the spindle at those locations. Preferably, end surface 59 of main body 10 can be swaged so as to prevent withdrawal of spindle 12 from within main body 10 so far as to inadvertently release detent ball arrangement 50, or to disengage threads T1 or T2.

It can be appreciated that the exemplary preferred embodiment thus described provides a relatively simple device that can be easily adjusted to allow an accurate depth of cut by blade 11. Spindle 12 is turned in body 10 to position front end 18 thereof at the first index mark 16 across the index window 15. The chuck clamp actuator 22 is lifted raising the chuck clamp 40 and allowing the chuck 30 to release or open. Blade 11 can then be inserted into the slot 24 on sloped surface 20 of body 10 and thence into slot 33 in the jaws 34 of collet 30. Initial positioning of blade 11 can then be effected by placing a flat preferably nonmetallic object against surface 20 of body 10 with the knife oriented so as to permit blade 11 to rest against this flat object flush with the surface 20. The actuator 22 is then depressed thereby locking blade 11 into chuck 30 in the zero depth of cut position.

The desired depth of cut can then be adjusted by turning spindle 12 in the appropriate direction. Typically, the threads will be such as require a clockwise rotation of spindle 12 as viewed from the rear of body 10. A full turn of spindle 12 causes spindle 12 to advance into the body 10 one thread pitch P1 of threads T1. At the same time, the externally threaded T2 chuck 30 is retracted into the internally threaded spindle 12 one T2 thread pitch (P2). Therefore chuck 30 and thus blade 11 advances only P1 minus P2 for each revolution of spindle 12. As mentioned previously, the blade cutting edge exposure E is proportional to the axial blade advancement times the sine of the angle a which cutting edge 17 and sloped body surface 20 make with the center line of housing 10. By selecting the proper combination of thread pitches and blade angle, the blade exposure per full turn can be set at any desired measurement such as 0.001 inches or 0.1 millimeters. Also the setting of the blade 11 exposure is easily read at the index window 15 because index marks 16 can be spaced equal to one-half or one pitch of the spindle to body threads 26 and 28 (T1) which is far enough apart to be discerned by normal vision. Further, the adjustment range of the knife can be incrementally extended by installing the blade at a preselected exposure E such as one or two full scale measurements while spindle 12 is at zero.

As mentioned, spindle 12 is detented to the body 10 as illustrated for quarter turns by detent ball assembly 50 installed in hole 48 of spindle 12. This ball 51 cooperates with four equally spaced detent grooves broached into the inner surface of body 10 as shown in FIGS. 3 and 8. If each half turn of the spindle 12 increases the blade exposure and cutting depth by 0.001 inches, then each successive detent thus increases the exposure by 0.0005 inches. Also each half turn of spindle 12 advances the front edge 18 of the spindle 12 by one index space 16 in index window 15. The index 16 or measurement scale is a typical easily read decimal scale in any desired configuration. For example, 1's may be marked as minor lines, increments of five with intermediate lines and 10's with major lines. In a typical embodiment, full scale is 40 spaces or 0.040 inch depth of cut. The depth of cut can be incrementally increased by installing the blade with a preselected exposure while the spindle is set at zero as mentioned. Thus if the blade is installed with a 0.040 inch exposure, each additional 0.001 inch of adjustment would be added to this 0.040 starting increment. In a typical application, the preferred embodiment as shown and described can permit up to 0.120 inches of blade exposure and still hold the blade firmly.

It is readily apparent that blade 11 can be easily changed and a new blade inserted. Spring 46 further holds the threads as between chuck 30, spindle 12 and body 10 in tension thereby eliminating thread backlash, this in addition to biasing the chuck actuator 22 and thus clamp 40 in the locked position. Although blade 11 has been shown with a continuous single cutting edge 17, the invention is well suited for use with a wide variety of blades when applied as a knife. For instance edge 17 could be serrated which is more useful for long flat cutting such as paper on a flat surface.

In assembly, the knife as shown is typically staked in the assembled condition. This is to prevent backing spindle 12 out too far and losing the ball detent assembly 50 and prevents disturbance of the proper axial relationship of the cooperating threads as between body 10, spindle 12 and collet 30. This staking can be realized by swaging end surface 59 of body 10.

For a typical assembly procedure of a device in accordance with the preferred embodiment shown, the chuck 30 is initially threaded into spindle 12 for a preselected exact distance. A long, narrow leader blade, not shown, is then temporarily placed in slot 33 of chuck 30 and a chuck clamp 40 placed in position on chuck 30. This entire assembly is inserted into body 10 with the leader blade extending outwardly through the slot 24 of sloped front surface 20. Spindle 12 is then threaded into body 10. Actuator spring 46 is then inserted through the bore 45 in the front of slope surface 20. Chuck clamp actuator 22 is rotated approximately 90° clockwise from its installed position and inserted into slot 24 of body 10 so as to engage the front edge of spring 46. Spring 46 is then compressed by the rear edge of actuator 22 and thence actuator 22 is moved downwardly until slot 37 slips over pin 36 in slot 33 of section 35 in chuck 30. Actuator 22 is pivoted into slot 33 of chuck 30 and moved forwardly until slot 38 thereof engages slot 42 of chuck clamp 40. Spindle 12 can then be backed out of body 10 until hole 48 is exposed at which point detent ball assembly 50 is inserted therein and spindle 12 returned within body 10. Plastic cap 25 can then be installed. Note that if an orienting groove 26 is included on cap 25, means should be included for insuring that cap 25 is attached in proper relation to spindle 12. The actuator 22 can then be raised so as to release clamp 40 thus permitting removal of the alignment or leader blade held by jaws 34.

Although the present invention has been described with particularity relative to the foregoing exemplary preferred embodiment, various changes, modifications, applications and additions will be readily apparent to those having normal skill in the art without departing from the spirit of this invention.

What is claimed is:

1. Apparatus for providing precise linear positioning of a member comprising:

housing means having a cylindrical threaded portion thereon, spindle means having first and second cylindrical threaded sectors in spaced relation thereon with said first threaded sector being arranged for cooperative engagement with said threaded portion of said housing means, chuck means including means at one end for gripping the member and a cylindrically threaded segment at the other end for cooperatively engaging said second cylindrical threaded sector of said spindle means, the threads of said segment and said second sector being of a smaller pitch but common direction relative to the threads of said housing means and said first sector, and means retaining said chuck means for permitting axial movement thereof relative to said housing means while preventing rotary motion between said chuck means and said housing means, said retaining means including means extending through and externally accessible from said housing means for releasably engaging said gripping means with the member, whereby application of relatively large rotary motion to said spindle means results in relatively small linear motion of the member gripped by said chuck means.

2. Apparatus in accordance with claim 1 wherein said chuck means includes a slot extending thereinto for said one end with said slot being oriented transverse to the axis of said housing means, said gripping means further including wedge means engaging the sidewalls of said chuck means on either side of said slot for selectably urging said sidewalls for closing said slot thereby clamping the member within said slot.

3. Apparatus in accordance with claim 2 wherein said retaining means is a substantially flat lever pivotally attached within said slot of said chuck means and extending externally through a channel in said housing means, said wedge means being attached to said lever means whereby release or clamping of the member within said slot of said chuck means can be selectably controlled by said lever.

4. Apparatus in accordance with claim 3 which further includes means for biasing said lever in a direction tending to force said wedge means into clamping relation to said chuck means whereby release of the member is effected by outwardly pivoting said lever relative to said housing means.

5. Apparatus in accordance with claim 4 wherein said housing means has a plurality of axial grooves, said apparatus further including spring-biased means retained within said spindle means for cooperating with said axial grooves as a detent.

6. Apparatus in accordance with claim 1 for precise positioning of a member which is an elongated tool having a shank terminating in a work edge on one end oriented at an angle "a" relative to the length of the tool shank, said chuck means gripping end including a pair of resilient jaws in spaced parallel relation for receiving the tool shank and means for forcing said jaws into engagement with the tool shank, said housing means being adapted for internally and coaxially containing said chuck means, said housing means terminating at one end in a flat surface sloped at an angle $a$ relative to the axis of said housing means and having a slot through said flat surface for accommodating exit and egress of the tool work edge therethrough, whereby the amount of extension of the tool work edge relative to said flat surface externally to said housing means via movement through said slot is determined by the sine of the angle $a$ and the difference in pitch between said first and second threaded sectors.

7. Apparatus in accordance with claim 6 wherein said housing means has an elongated opening through the sidewall thereof with said opening being parallel to the axis of said housing means, said housing means further having a plurality of graduation marks arrayed in proximity to said opening, said spindle means having at least one reference line thereon visible through said opening in conjunction with said graduation marks for indicating the amount of external extension of the tool work edge.

8. Apparatus for precision positioning of a knife blade having a sloped working edge comprising:
   a generally tubular housing having at one end a front surface sloped relative to the axis thereof at an angle substantially in conformity with the slope of the blade working edge, said housing having a bore extending thereinto from the other end,
   spindle means arranged to enter said housing bore,
   a first thread engagement for providing cooperative engagement between said spindle means and said housing whereby rotary motion of said spindle means effects linear movement thereof relative to the axis of said housing,
   clamping means having parallel jaws extending from a shank portion so as to define a slot between said jaws, said clamping means being adapted to fit within said housing bore,
   a second thread arrangement for providing cooperative engagement between said clamping means shank portion and said spindle means whereby rotary motion of said spindle means effects linear motion of said clamping means relative to the axis of said housing in a smaller amount and opposite direction relative to the linear motion of said spindle means,
   a generally L-shaped lever arm pivotally attached at one end thereof within said slot of said clamping means and having the other end thereof extending through a channel in said housing means thereby permitting linear axial movement of said clamping means while preventing rotary motion thereof,
   wedge means attached to said lever arm within said housing for urging said jaws of said clamping means in a closing direction whereby the sides of the shank of the knife blade can be selectably gripped in said clamping means slot, and
   means biasing said lever arm around the pivotal attachment thereof for normally urging said wedge means into a closure position relative to said clamping means jaws, whereby said lever arm is accessible externally to said housing for pivoting against said biasing means thereby releasing the knife blade whereas rotation of said spindle means will effect precise axial linear motion of the knife blade relative to said housing.

9. Apparatus in accordance with claim 8 wherein said housing means further includes means cooperating with said spindle means for providing a calibrated indication of the linear position of the blade.

\* \* \* \* \*